United States Patent [19]

George et al.

[11] Patent Number: 4,925,850
[45] Date of Patent: May 15, 1990

[54] DERIVATIVES OF 2-((4-PIPERIDINYL)METHYL)-1,2,3,4-TETRAHYDROISOQUINOLINE, THEIR PREPARATION AND THEIR APPLICATION IN THERAPEUTICS

[75] Inventors: Pascal George, St. Arnoult en Yvelines, Belgium; Mireille Sevrin, Paris, France; Christian Maloizel, Meudon, France; Arlette Tixidre, Gif sur Yvette, France; Jacques Froissant, Moree, France

[73] Assignee: Synthelabo, Paris, France

[21] Appl. No.: 306,497

[22] Filed: Feb. 6, 1989

[30] Foreign Application Priority Data

Jul. 12, 1988 [FR] France .................. 88 09447

[51] Int. Cl.$^5$ .................. A61K 31/47; C07D 217/04
[52] U.S. Cl. .................. 514/307; 546/146; 546/149
[58] Field of Search .................. 546/146, 149; 514/307

[56] References Cited

U.S. PATENT DOCUMENTS

| | | | |
|---|---|---|---|
| 3,634,410 | 1/1972 | Tvaermose et al. | 260/293.64 |
| 3,836,536 | 9/1974 | Morrison et al. | 546/146 |
| 4,220,778 | 9/1980 | Ellefson et al. | 546/146 |
| 4,261,998 | 4/1981 | Najer | 546/146 |
| 4,766,131 | 8/1988 | Davidson et al. | 546/149 |

OTHER PUBLICATIONS

George, et al., "Chemical Abstracts", vol. 110, 1989, col. 110:231451d.

*Primary Examiner*—Richard L. Raymond
*Assistant Examiner*—James H. Turnipseed
*Attorney, Agent, or Firm*—Fleit, Jacobson, Cohn, Price, Holman & Stern

[57] ABSTRACT

A compound of formula (I):

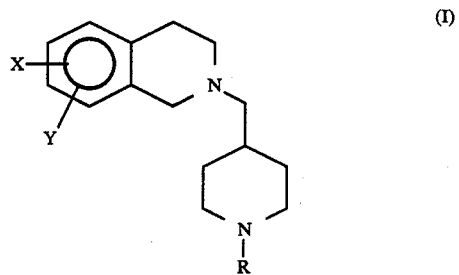

in which:
X is hydrogen or a methyl or methoxy group;
Y is a halogen or a methyl or methoxy group; and
R is a group of formula —Z—R' in which:
Z is a —$CH_2$— group, and
R' is a phenyl group unsubstituted or substituted by one, two or three substituents selected from halogen atoms and trifluoromethyl, linear or branched ($C_1$-$C_3$) alkyl and linear or branched ($C_1$-$C_3$) alkoxy groups;

or a pharmacologically acceptable acid addition salt thereof.

7 Claims, No Drawings

DERIVATIVES OF 2-((4-PIPERIDINYL)METHYL)-1,2,3,4-TETRAHYDROISOQUINOLINE, THEIR PREPARATION AND THEIR APPLICATION IN THERAPEUTICS

The present Patent Application relates to derivatives of 2-[(4-piperidinyl)methyl]-1,2,3,4-tetrahydroisoquinoline, their preparation, compositions containing them and their application in therapy.

This Application is related to copending, commonly assigned Ser. No. 07/228,748, filed Aug. 5, 1988, now U.S. Pat. No. 4,885,302 which relates to compounds of the formula:

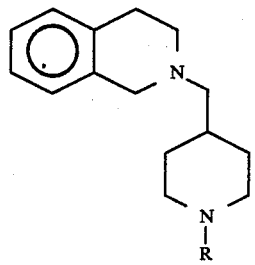

in which: R is hydrogen, a methyl group, a benzyl group unsubstituted or substituted by a chlorine atom or by a methyl or methoxy group, or a phenethyl group.

The present application provides a compound of formula (I):

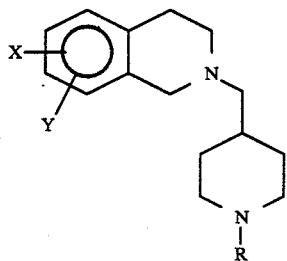

in which:
X is hydrogen or a methyl or methoxy group;
Y is a halogen or a methyl or methoxy group; and
R is a group of formula —Z—R' in which:
Z is a —CH$_2$— or —CO— group, and
R' is a phenyl group unsubstituted or substituted by one, two or three substituents selected from halogen, for example chlorine, atoms and trifluoromethyl, linear or branched (C$_1$–C$_3$) alkyl, for example methyl or ethyl, and linear or branched (C$_1$–C$_3$) alkoxy, for example ethoxy, groups;
or a pharmacologically acceptable acid addition salt thereof.

The X group is generally in the 5- or 6-position. The Y group may be in the 5-,6-,7- or 8-position. The substituent on the phenyl group R is generally in the 3-position.

Examples of pharmacologically acceptable acid addition salts are hydrochloride, dihydrochloride, fumarate, difumarate and hemifumarate salts.

The compounds of formula (I) may be prepared by the process illustrated in Scheme 1 given hereinafter.

The present invention also provides a process for preparing a compound of formula (Ib) as shown in Scheme 1, or a pharmacologically acceptable acid addition salt thereof, in which X, Y and R' are as defined above, which comprises reducing a compound of formula (Ia) as shown in Scheme 1 in which X, Y and R' are as defined above, with a simple or complex boron or aluminium hydride in an ethereal solvent at a temperature of from 20° to 100° C. and, if desired, forming a pharmacologically acceptable acid addition salt of the compound thus obtained.

Examples of suitable ethereal solvents are diethyl ether, tetrahydrofuran and dioxane. Examples of simple or complex boron or aluminium hydrides are lithium aluminium hydride, aluminium hydride, a diborane/tetrahydrofuran complex or a diborane/methyl sulphide complex. Other simple or complex boron or aluminium hydrides may be used.

The present invention further provides a process for preparing a compound of formula (Ia) as shown in Scheme 1, or a pharmacologically acceptable acid addition salt thereof, in which X, Y and R' are as defined above, which comprises reacting a compound of formula (II) as shown in Scheme 1 in which X and Y are as defined above, with a tosylate of formula (III) as shown in Scheme 1 in which Tos is a tosylate group and R' is as defined above, in the absence or presence of an inert solvent at a temperature of from 20° to 150° C. and, if desired, forming a pharmacologically acceptable acid addition salt of the compound thus obtained.

Examples of suitable inert solvents are dimethylformamide, toluene and xylene.

The reaction may, for example, be carried out in the presence of an organic or inorganic base, for example a tertiary amine or an alkali metal carbonate or bicarbonate.

The compound of formula (Ia) obtained by the process defined above may be used as the starting material for the process for preparing the compound of formula (Ib).

Scheme 1

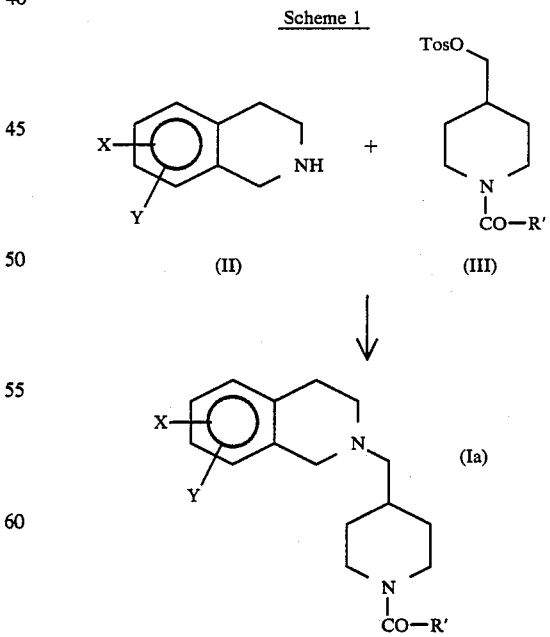

Scheme 1 (continued)

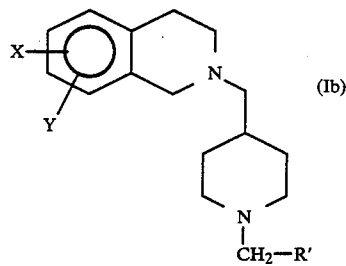

(Ib)

Scheme 2

[Structure IV: 4-piperidinemethanol with OH and NH] → [Structure V: with OCOR' and N-COR']

↓

[Structure VI: with OH and N-COR']

← (III)

1,2,3,4-Tetrahydroisoquinolines of formula (II) may be obtained by a process such as that described by D. J. Sall and G. L. Grunewald in J. Med. Chem., 1987, 30, 2208–2216, or by any analogous method.

Tosylates of formula (III) may be prepared, for example, according to a method illustrated in Scheme 2. 4-Piperidinemethanol of formula (IV) is reacted with an acid chloride of formula R'COCl, in which R' is defined as above, in an inert solvent such as a chlorinated solvent, at a temperature of from 20° to 80° C. to produce an ester-amide of formula (V). The ester-amide of formula (V) is saponified, for example with sodium or potassium hydroxide, in a lower aliphatic alcoholic solvent, preferably ethanol, to obtain an alcohol of formula (VI), which is converted to the tosylate thereof by reaction with tosyl chloride in a basic medium such as pyridine.

4-Piperidinemethanol of formula (IV) may be obtained, for example, by reduction of ethyl 4-piperidinecarboxylate with lithium aluminium hydride, or by reduction in such a manner of ethyl 1-benzyl-4-piperidinecarboxylate followed by catalytic hydrogenolysis under pressure.

Copending Ser. No. 07/228,748 describes various processes for the preparation of compounds of formula (I) except that X and Y each represent a hydrogen atom; it goes without saying that the principles of these processes are also applicable in the preparation of substituted compounds according to the present invention.

The following Examples illustrate the preparation of some compounds according to the invention. Elemental microanalyses and IR and NMR spectra confirm the structures of the products obtained.

The numbers indicated in brackets in the titles of the Examples correspond to those in the table that is given further on.

EXAMPLE 1

(Compound No. 16)

5,8-Dimethoxy-2-[[1-[(3-methylphenyl)carbonyl]-4-piperidinyl]methyl]-1,2,3,4-tetrahydroisoquinoline fumarate.

1.1. 4-Piperidinemethanol.

28.5 g (0.75 mole) of lithium aluminium hydride and 1.2 of tetrahydrofuran are placed in a 4 three-necked round-bottomed flask equipped with a mechanical stirring system and a condenser. 117.9 g (0.75 mole) of ethyl 4-piperidinecarboxylate dissolved in 1.2.1 of tetrahydrofuran are added to the resulting suspension and the mixture is stirred for 6h at 20° C. It is cooled to 0° C. then hydrolysed by successively adding 22 ml of water, 22 ml of 1N sodium hydroxide and 46 ml of water. The mixture is stirred for 30 min. at 20° C. and filtered, and the precipitate is washed with tetrahydrofuran then with ether. The solvents are evaporated under reduced pressure, and 84.4 g of an oil are obtained which is used just a it is in the following stage.

1.2. [1-(3-Methylbenzoyl)-4-piperidinyl]methyl 3-methylbenzoate.

42.25 g (0.367 mole) of 4-piperidinemethanol and 430 ml of 1,2-dichloroethane are placed under argon atmosphere in a 3 three-necked round-bottomed flask, and 82 g (0.81 mole) of triethylamine then 125.2 g (0.81 mole) of 3-methylbenzoyl chloride are added. The mixture is heated under reflux for 4h30, a further 8.2 g (0.08 mole) of triethylamine and 12.5 g (0.08 mole) of 3-methylbenzoyl chloride are added, and the mixture is heated for a further 3h.

The mixture is filtered, the salts are washed with 1,2-dichloroethane, the filtrate is evaporated under reduced pressure, the residue is dissolved in ethyl acetate, the solution is washed with a saturated aqueous solution of sodium chloride, the solvent is evaporated under reduced pressure, and the residue is recrystallised from a 1/1 isopropyl alcohol/ethyl acetate mixture. 80 g of a white solid are obtained. Melting point: 80°–83° C.

1.3. 1-(3-Methylbenzoyl)-4-piperidinemethanol.

A solution of 12.76 g (0.23 mole) of potassium hydroxide in 75 ml of ethanol and 75 ml of water is added to a solution of 80 g (0.23 mole) of [1-(3-methylbenzoyl)-4-piperidinyl]methyl 3-methylbenzoate in 400 ml of ethanol. The mixture is stirred at 20° C. for 3h, the solvent evaporated under reduced pressure and the aqueous phase is extracted with ethyl acetate. The organic phase is washed with water then with a saturated aqueous solution of sodium chloride, and dried over magnesium sulphate. The solvent is evaporated under reduced pressure and 53 g of an alcohol are obtained, which is used just as it is in the next stage.

1 4. [1-(3-Methylbenzoyl)-4-piperidinyl]methyl 4-methylbenzenesulphonate.

53.3 g (0.28 mole) of 4-methylbenzenesulphonyl chloride in 60 ml of pyridine are added to a solution of 52 g (0.22 mole) of 1-(3-methylbenzoyl)-4-piperidinemethanol in 100 ml of pyridine. The mixture is stirred at 20° C. for 4h, then poured into ice. The aqueous phase is extracted with dichloromethane, the organic phase is washed with a 10N aqueous solution of hydrochloric acid and dried over magnesium sulphate. The solvents are evaporated under reduced pressure and 70 g of a white solid are obtained. Melting point: 68°-70° C.

1.5. 5,8-Dimethoxy-2-[[1-[(3-methylphenyl)carbonyl]-4-piperidinyl]methyl]-1,2,3,4-tetrahydroisoquinoline fumarate.

A mixture of 3.86 g (0.02 mole) of 5,8-dimethoxy-1,2,3,4-tetrahydroisoquinoline and 8.5 g of [1-(3-methylbenzoyl)-4-piperidinyl]methyl 4-methylbenzenesulphonate is heated under argon atmosphere for 20h. Dichloromethane is added to the mixture then concentrated ammonia, the organic phase is separated, washed twice with water, dried over magnesium sulphate and filtered and the solvent is evaporated under reduced pressure. An oily residue is obtained, which is taken up with ether, an insoluble fraction is separated by filtration, the ether is evaporated and the residue is purified by chromatography on a column of silica, eluting with a 98/2 dichloromethane/methanol mixture. 3.3 g of pure base are isolated in this way.

1.6 g of this base are dissolved in the minimum amount of ethanol, 0.45 g of fumaric acid dissolved in 60 ml of ethanol are added, the ethanol is evaporated and the residue is recrystallised from isopropyl alcohol. 1.3 g of fumarate are ultimately isolated. Melting point: 156°-158° C.

EXAMPLE 2

(Compound No. 17)

5,8-Dimethoxy-2-[[1-[(3-methylphenyl)methyl]-4-piperidinyl]methyl]-1,2,3,4-tetrahydroisoquinoline difumarate. 0.29 g (0.0078 mole) of lithium aluminium hydride are added to a solution of 1.6 g (0.0038 mole) of 5,8-dimethoxy-2-[[1-[(3-methylphenyl)carbonyl]-4-piperidinyl]-methyl]-1,2,3,4-tetrahydroisoquinoline in 30 ml of ether, the mixture is stirred for 3h at room temperature, cooled in an ice bath and hydrolysed with 2.4 ml of 1N sodium hydroxide. The mixture is filtered and the filtrate is evaporated, yielding 1.4 g of base. The latter is dissolved in the minimum amount of ethanol, 0.82 g of fumaric acid dissolved in 100 ml of ethanol are added, the ethanol is evaporated and the residue is recrystallised from isopropyl alcohol. 1.5 g of difumarate are ultimately isolated. Melting point: 198°-201° C.

The following table illustrates the chemical structures and the physical properties of some of the compounds according to the invention.

In the last column "(d)" indicates decomposition of the compound at the melting point.

TABLE

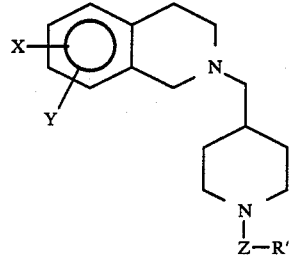

| No | X | Y | Z | R' | Salt* | m.p. (°C.) |
|----|-------|--------|-----|------------|-------|------------|
| 1 | H | 5-CH$_3$ | CO | C$_6$H$_5$— | HCl | 211-212 |
| 2 | H | 5-CH$_3$ | CH$_2$ | C$_6$H$_5$— | difum. | 194-196 |
| 3 | H | 5-CH$_3$ | CO | 3-ClC$_6$H$_4$— | HCl | 214-216 |
| 4 | H | 5-CH$_3$ | CH$_2$ | 3-ClC$_6$H$_4$— | difum. | 206-208 |
| 5 | H | 5-CH$_3$ | CO | 3-C$_2$H$_5$OC$_6$H$_4$ | HCl | 179-182 |
| 6 | H | 5-CH$_3$O | CO | C$_6$H$_5$— | HCl | 230(d) |
| 7 | H | 5-CH$_3$O | CH$_2$ | C$_6$H$_5$— | difum. | 188-190 |
| 8 | H | 5-CH$_3$O | CO | 3-ClC$_6$H$_4$— | fum. | 168-170 |
| 9 | H | 6-CH$_3$O | CO | C$_6$H$_5$— | HCl | 183-185 |
| 10 | H | 8-CH$_3$O | CO | C$_6$H$_5$— | HCl | 205-215(d) |
| 11 | H | 8-CH$_3$O | CH$_2$ | C$_6$H$_5$— | difum. | 198-201 |
| 12 | 5-CH$_3$O | 8-CH$_3$O | CO | C$_6$H$_5$— | HCl | 240-246(d) |
| 13 | 5-CH$_3$O | 8-CH$_3$O | CH$_2$ | C$_6$H$_5$— | difum. | 193-197 |
| 14 | 5-CH$_3$O | 8-CH$_3$O | CO | 3-ClC$_6$H$_4$— | fum. | 151-152 |
| 15 | 5-CH$_3$O | 8-CH$_3$O | CH$_2$ | 3-ClC$_6$H$_4$— | difum. | 200-202 |
| 16 | 5-CH$_3$O | 8-CH$_3$O | CO | 3-CH$_3$C$_6$H$_4$— | fum. | 156-158 |
| 17 | 5-CH$_3$O | 8-CH$_3$O | CH$_2$ | 3-CH$_3$C$_6$H$_4$— | difum. | 198-201 |
| 18 | 5-CH$_3$O | 8-CH$_3$O | CO | 3-C$_2$H$_5$OC$_6$H$_4$— | ½fum | 134-135 |
| 19 | 5-CH$_3$O | 8-CH$_3$O | CH$_2$ | 3-C$_2$H$_5$OC$_6$H$_4$— | difum. | 178-180 |
| 20 | 5-CH$_3$O | 8-CH$_3$O | CH$_2$ | 3-CF$_3$C$_6$H$_4$— | difum. | 193-203(d) |
| 21 | 6-CH$_3$O | 7-CH$_3$O | CO | C$_6$H$_5$— | fum. | 138-139 |
| 22 | H | 6-Cl | CO | C$_6$H$_5$— | HCl | 222-225 |
| 23 | H | 6-Cl | CH$_2$ | C$_6$H$_5$— | difum. | 136-139 |

TABLE-continued

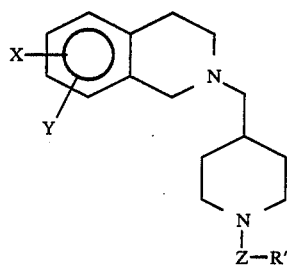

| No | X | Y | Z | R' | Salt* | m.p. (°C.) |
|----|---|------|----|--------|------|-----------|
| 24 | H | 8-Cl | CO | C₆H₅— | HCl | 198–200 |

*HCl, fum., difum. and ½fum. respectively designate a hydrochloride, a fumarate, a difumarate and a hemifumarate.

The compounds of the invention have been subjected to a series of pharmacological tests which have shown their value as therapeutically active substances.

Thus, their affinity for the type 5-HT$_{1A}$ serotoninergic receptors has been the subject of a study. In the hippocampus of the rat, the compounds displace a specific marked ligand, [$^3$H]-8-hydroxy-2-dipropylaminotetralin (hereafter called "[$^3$H]-8-OH-DPAT") described by Gozlan et al., Nature, (1983), 305, 140–142.

The animals used are male Sprague-Dawley rats weighing 160 to 200 g. After decapitation the brain is removed and the hippocampus excised. The tissue is ground in an Ultra-Turrax Polytron apparatus for 30 s at half the maximum speed in 10 volumes of 50 mM Tris buffer whose pH is adjusted to 7.4 with hydrochloric acid (i.e. 100 mg of fresh tissue per ml). The homogenised tissues are washed three times at 4° C., centrifuging them each time at 48000×g and re-suspending the pellet for 10 min. in fresh cooled buffer. Ultimately the last pellet is suspended in the buffer to achieve a concentration of 100 mg of original tissue per ml of 50 mM buffer. The suspension is left to incubate at 37° C. for 10 min. The binding with [$^3$H]-8-OH-DPAT is determined by incubation of 10 μl of the suspension of membranes in a final volume of 1 ml of buffer containing 10 μM of pargyline. After incubation the membranes are recovered by filtration through Whatman GF/B filters that are washed three times with 5-ml aliquot quantities of ice-cold buffer. The filters are extracted in scintillation liquid and their radioactivity is measured by liquid scintigraphy. The specific binding with [$^3$H]-8-OH-DPAT is defined as the radioactive quantity retained on the filters and which can be inhibited by co-incubation in 10 μM 5-hydroxytryptamine. At a concentration of 1 nM of [$^3$H]-8-OH-DPAT the specific binding represents 70 to 80% of the total radioactivity recovered on the filter.

The percentage inhibition of binding with [$^3$H]-8-OH-DPAT is determined for each concentration of compounds studied, then the IC$_{50}$ concentration, the concentration at which there is 50% inhibition of binding.

The IC$_{50}$ values for the compounds of the invention are between 0.001 and 0.3 μM.

The central activities of the compounds of the invention have been evaluated by their effects on the "PGO (pontogeniculo-occipital) spikes" induced by reserpine (PGO-R test) in cats, following the method described by H. Depoortere, Sleep 1976, 3rd Europ. Congr. Sleep Res., Montpellier 1976, 358–361 (Karger, Basel 1977). Cumulative doses of the compounds to be studied are administered (from 0.003 to 3 mg/kg intravenously) at 30 min. intervals, 4h after intraperitoneal injection of a 0.75 mg/kg dose of reserpine, to curarised cats receiving artificial ventilation. The electroencephalographic and phasic activities are picked up (PGO-R spikes) by means of cortical and deep electrodes (lateral geniculate bodies). The percentage reduction in the number of PGO spikes is determined for each dose of compound studied, then the AD$_{50}$, the active dose that reduces the number of spikes by 50%. The ED$_{50}$ values for the compounds of the invention are between 0.003 and 3 mg/kg administered intravenously.

The test results show that compounds of general formula (I) possess a great affinity and selectivity, in vitro, for the type 5-HT$_{1A}$ serotoninergic receptors. In vivo they exhibit an agonistic, partial agonistic or antagonistic activity at the level of these receptors.

The compounds of the invention may hence be used for the treatment of illnesses and diseases directly or indirectly involving the type 5-HT$_{1A}$ serotoninergic receptors, particularly for the treatment of depressive conditions, anxiety conditions, sleep disorders, for the regulation of food intake, and for the treatment of vascular, cardiovascular or cerebrovascular conditions such as hypertension or migraine.

Accordingly the present invention provides a compound of formula (I), or a pharmacologically acceptable acid addition salt thereof, for use in a method of treatment of the human or animal body by therapy, especially for use in a method for the treatment of a depressive condition, a sleep disorder, a vascular, cardiovascular or cerebrovascular condition, an anxiety condition or for use in the regulation of food intake.

The present invention additionally provides the use of a compound of formula (I), or a pharmacologically acceptable acid addition salt thereof, in the manufacture of a medicament for the treatment of a depressive condition, a sleep disorder, a vascular, cardiovascular or cerebrovascular condition, an anxiety condition or for use in the regulation of food intake.

The compounds of the invention may be presented in any appropriate form for oral or parenteral administration, made up with suitable excipients, and assayed to allow a daily dosage of, for example, 1 to 1000 mg. Accordingly the present invention also provides a pharmaceutical composition which comprises a compound of formula (I), or a pharmacologically acceptable acid addition salt thereof, and a pharmaceutically acceptable excipient.

We claim:

1. A compound of formula (I):

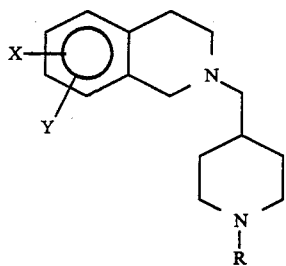

in which:

X is hydrogen or a methyl or methoxy group;
Y is a halogen or a methyl or methoxy group; and
is a group of formula —Z—R' in which:
Z is a —CH$_2$— or —CO— group, and
R' is a phenyl group unsubstituted or substituted by one, two or three substituents selected from halogen atoms and trifluoromethyl, linear or branched (C$_1$-C$_3$) alkyl and linear or branched (C$_1$-C$_3$) alkoxy groups;

or a pharmacologically acceptable acid addition salt thereof.

2. A compound according to claim 1 in which X is hydrogen or a 5-methoxy or 6-methoxy group.

3. A compound according to claim 1 in which Y is a 5-methyl, 5-methoxy, 6-methoxy, 7-methoxy or 8-methoxy group or 6-chloro or 8-chloro.

4. A compound according to claim 1 in which R' is a phenyl group unsubstituted or substituted in the 3 position by chlorine or by methyl, ethoxy or trifluoromethyl group.

5. A compound according to claim 1 which is in the form of a hydrochloride, dihydrochloride, fumarate, difumarate or hemifumarate salt.

6. A pharmaceutical composition which comprises a pharmaceutically effective amount of a compound as defined in claim 1 and a pharmaceutically acceptable excipient.

7. A method for the treatment of a depressive condition, a sleep disorder, a vascular, cardiovascular or cerebrovascular condition, an anxiety condition or for the regulation of food intake, which comprises administering to a subject in need of such treatment an effective amount of a compound as defined in claim 1.

* * * * *